United States Patent [19]

Richmond

[11] Patent Number: 4,919,667
[45] Date of Patent: Apr. 24, 1990

[54] IMPLANT

[75] Inventor: James W. Richmond, Kalamazoo, Mich.

[73] Assignee: Stryker Corporation, Kalamazoo, Mich.

[21] Appl. No.: 279,558

[22] Filed: Dec. 2, 1988

[51] Int. Cl.$^5$ .............................................. A61F 2/30
[52] U.S. Cl. ......................................... 623/18; 623/20
[58] Field of Search .................... 623/16, 18, 13, 11, 623/20, 22, 23, 66

[56] References Cited

U.S. PATENT DOCUMENTS

| | | | |
|---|---|---|---|
| 3,867,728 | 2/1975 | Stubstad et al. | 623/18 |
| 3,879,767 | 4/1975 | Stubstad | 623/18 |
| 3,886,600 | 6/1975 | Kahn et al. | 623/18 |
| 3,938,198 | 2/1976 | Kahn et al. | 623/18 |
| 3,971,670 | 7/1976 | Homsy | 623/18 |
| 3,992,725 | 11/1976 | Homsy | 623/18 |
| 4,085,466 | 4/1978 | Goodfellow et al. | 623/18 |
| 4,127,902 | 12/1978 | Homsy | 623/18 |
| 4,129,470 | 12/1978 | Homsy | 623/18 |
| 4,224,696 | 9/1980 | Murray et al. | 623/18 |
| 4,224,697 | 9/1980 | Murray et al. | 623/18 |
| 4,344,193 | 8/1982 | Kenny | 623/18 |
| 4,502,161 | 3/1985 | Wall | 623/18 |

FOREIGN PATENT DOCUMENTS

| | | | |
|---|---|---|---|
| 1201853 | 3/1986 | Canada | 623/18 |
| 1201854 | 3/1986 | Canada | 623/18 |
| 1201855 | 3/1986 | Canada | 623/18 |
| 637118 | 12/1978 | U.S.S.R. | 623/18 |

Primary Examiner—Richard J. Apley
Assistant Examiner—David J. Isabella
Attorney, Agent, or Firm—Flynn, Thiel, Boutell & Tanis

[57] ABSTRACT

A soft tissue implant in the form of a meniscus cartilage replacement for a patient. Appropriately shaped top and bottom layers sandwich therebetween at least one intermediate felted layer. A resilient bonding material coats the layers and holds same in a laminated condition. The intermediate layer(s) is cut narrower than the top and bottom layers and the layers have a common side edge. The top layer is contoured, to provide a wedge shaped cross section and a contoured three dimensional shape. A fabric member is bonded to the thickened edge of the laminant and is porous to invite ingrowth of patient tissue to anchor the implant eventually in place. In addition, a method of making the implant involves coating of layers with a resilient bonding material, applying the layers one atop the next, and curing the resilient bonding material after each successive layer is applied.

10 Claims, 2 Drawing Sheets

U.S. Patent    Apr. 24, 1990    Sheet 1 of 2    4,919,667
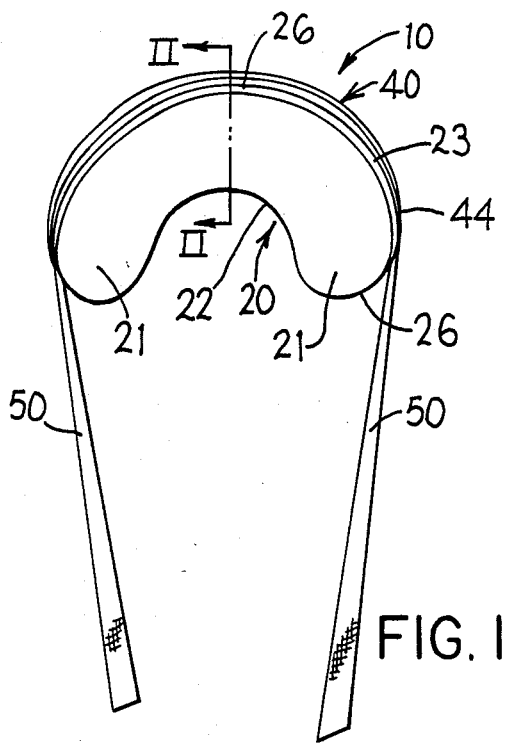
FIG. 1
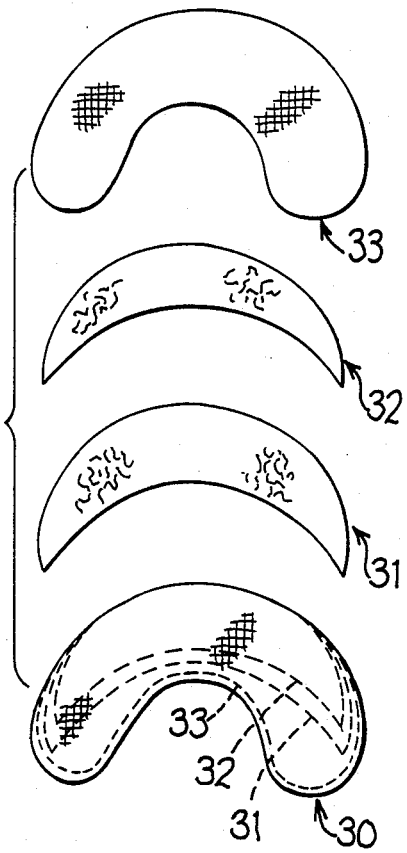
FIG. 3
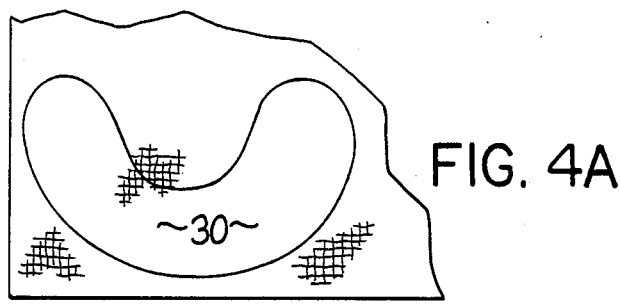
FIG. 4A
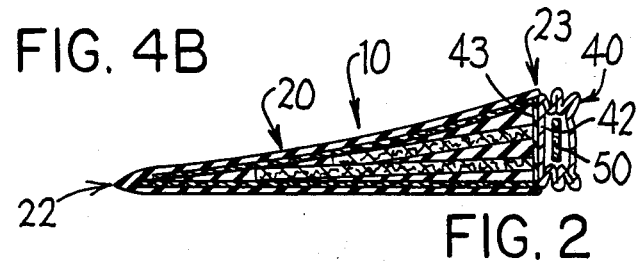
FIG. 2
FIG. 4B
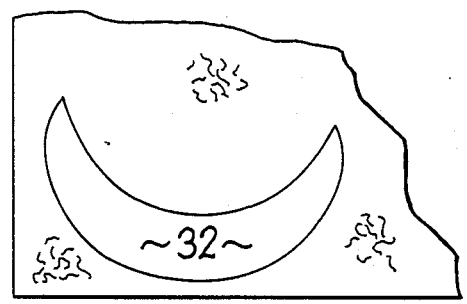
FIG. 5A
FIG. 5B

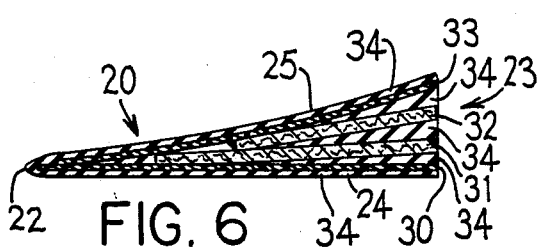
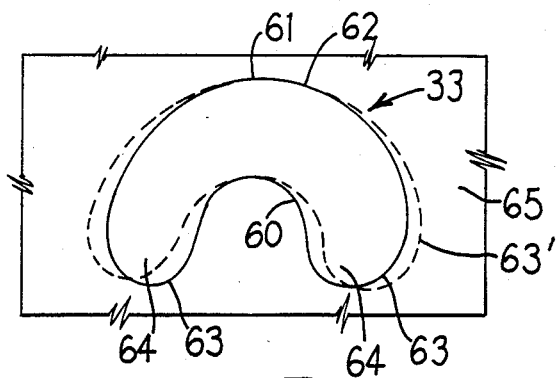
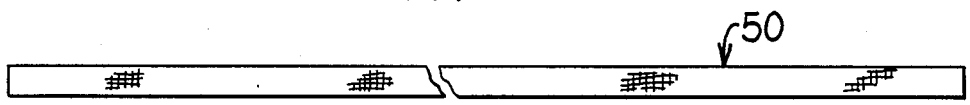
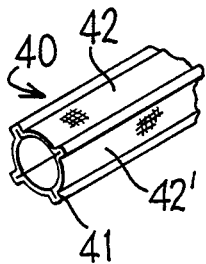
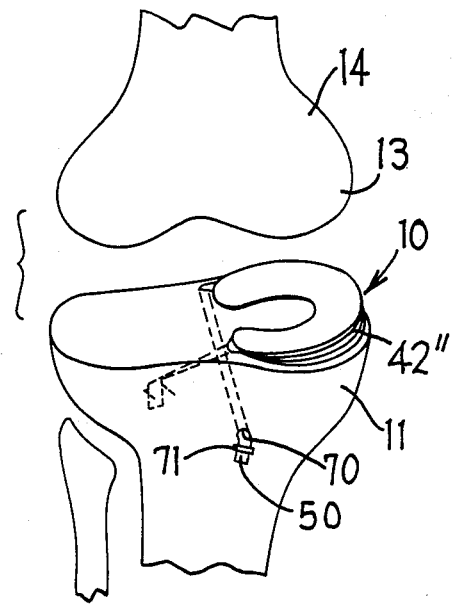

IMPLANT

FIELD OF THE INVENTION

This invention relates to a soft tissue implant and more particularly to a meniscus cartilage replacement for a patient.

BACKGROUND OF THE INVENTION

Wall U.S. Pat. No. 4,502,161 discloses a meniscus cartilage replacement for a patient which consists of a woven fiber sheet coated with a resilient material with a lateral extension of the sheet extending outside the joint for anchoring to the side of the tibia with a screw. However, the Wall replacement is thin and flat (two dimensional) and hence is non-anatomical in shape.

The following several patents are several of the references in the aforementioned Wall patent.

Kenny U.S. Pat. No. 4,344,193 discloses a meniscus cartilage replacement of three dimensional shape. However, the Kenny replacement consists simply of a non-reinforced molded silicone rubber member. Although other possible ways are mentioned briefly in passing, the Kenny drawings show sutures and increased thickness ends as ways to hold the replacement in place in the joint, the increased thickness ends being discussed in detail.

Stubstad U.S. Pat. No. 3,879,767 discloses an artificial implant but formed as a wrist replacement.

Homsy U.S. Pat. Nos. 3,971,670 and 4,127,902 are not references in the above Wall patent merely disclose artificial tension members which may be led through holes in bone and stapled for use as replacement tendons and ligaments. No cartilage replacement is shown.

In so far as I am aware a fully satisfactory meniscus cartilage replacement has not been achieved in the prior art.

Accordingly, the objects and purposes of the invention include provision of a soft tissue implant in the form of a meniscus cartilage replacement for a patient, which combines an anatomical shape with woven and felted fiber interior reinforcement for strength and durability, in which coated top and bottom surfaces are capable of sliding with respect to adjacent tissues of the patient in a manner to simulate a natural meniscus cartilage, in which a convex, exterior edge is capable of receiving natural fibrous tissue ingrowth of the patient to, in time, naturally anchor the implant in the joint of the patient and in which, optionally, the implant can be positively anchored to adjacent bone while awaiting such natural fibrous tissue ingrowth.

Other objects and purposes of the invention will be apparent to persons acquainted with apparatuses of the general type upon reading the following specification and inspecting the accompanying drawings.

SUMMARY OF THE INVENTION

The objects and purposes of the invention are met by providing a soft tissue replacement implant, such as a meniscus cartilage replacement, for a patient, which comprises appropriately shaped top and bottom layers sandwiching therebetween at least one intermediate felted layer, and a resilient bonding material coating the layers and holding same in a laminated condition. The intermediate layer(s) is cut narrower than the top and bottom layers and the layers have a common side edge. The top layer being contoured, to provide a wedge shaped cross section and a contoured three dimensional shape. A fabric member is bonded to the thickened edge of the resulting laminant and is porous to invite ingrowth of patient tissue to anchor the implant eventually in place. In addition, a method of making the implant involves coating of layers with a resilient bonding material, applying the layers one atop the next, and curing the resilient bonding material after each successive layer is applied.

BRIEF DESCRIPTION OF THE DRAWINGS

FIG. 1 is a pictorial view taken from the top and convex, exterior perimeter edge of a meniscus cartilage implant embodying the invention;

FIG. 2 is an enlarged cross sectional view substantially taken on the line II—II of FIG. 1;

FIG. 3 is an exploded view of woven and felted components of the FIG. 1 implant;

FIG. 4A is a top view of a fragment of woven fabric superimposed by the outline of one of the FIG. 3 components;

FIG. 4B is an edge view of the FIG. 4A sheet;

FIG. 5A is a top view of a sheet of felted material superimposed by the outline of a corresponding FIG. 3 component;

FIG. 5B is an edge view of the FIG. 5A felted sheet;

FIG. 6 is a fragment of the FIG. 2 cross sectional view but in an unfinished state;

FIG. 7 shows in dotted lines a top view of the top woven layer component of the FIG. 1 implant in a flat state, such component as shown in solid line being distorted into a three dimensional bowl segment shape;

FIG. 8 is a top view of a tube of the FIG. 1 implant;

FIG. 9 is a fragmentary pictorial view of an end portion of the FIG. 8 tube prior to trimming;

FIG. 10 is a top view of an optional elongate tape of the FIG. 1 implant;

FIG. 11 is a schematic pictorial view showing a FIG. 1 implant installed as a replacement for the natural medial meniscus cartilage in the knee joint of a patient.

DETAILED DESCRIPTION

FIG. 1 shows a soft tissue implant 10 embodying the invention.

Although the present invention in its broader aspects is applicable to implants in other portions of the body of a human (or other mammal) patient, for convenience of illustration of a preferred embodiment, the particular implant 10 here shown is adapted for replacement of a meniscus cartilage in a human knee. The present invention is readily applicable to both the lateral and medial meniscus cartilages, but for convenient illustration, the embodiment shown is a replacement for the medial meniscus cartilage.

Thus in FIG. 11, an implant 10 embodying the invention is shown installed atop the tibia 11 and below the corresponding condyle of the femur 14 of a patient.

The medial meniscus cartilage implant 10 is anatomically shaped, namely three dimensionally shaped like the natural medial meniscus cartilage of the patient.

More particularly then, the implant 10 is a generally C-shaped (or kidney bean shaped) implant as seen in FIG. 1 and is of wedge shaped central cross section, as shown in FIG. 2.

The implant 10 comprises a body 20 having spaced apart ends. The body 20 has a perimeter edge 22, 23 comprising a concave perimeter edge 22 and a convex perimeter edge 23 (FIGS. 1 and 6). The convex perimeter edge 23 defines the ends 21 of the generally C-shaped body 20. The concave and convex perimeter edges are oppositely facing and spaced across the width of the generally C-shaped body 20. The body 20 has a flat bottom face 24 (FIG. 6) and a sloped, preferably slightly concavely curved top surface 25. The central portion of the convex perimeter edge 23 is much thicker than the concave perimeter edge 22. For example, the central portion of the convex perimeter edge 23 may be about one-quarter inch high, whereas the concave perimeter edge is preferably a feather edge. The convex perimeter edge 23, at least in the central portion thereof, upstands substantially perpendicular from the bottom surface 24 of the body 20. The convex perimeter edge 23 tapers from the thick central portion 26 thereof toward the ends 21 of the body 20 (as can be generally seen in FIG. 11), so that the convex perimeter edge 23 tapers substantially to a feather edge in the central portion 26 of the ends 21.

The body 20 (FIG. 6) is a multi-layer laminate. In the preferred embodiment shown, such laminate comprises a woven cloth bottom layer 30 (FIGS. 3 and 4), and in successively stacked relation there atop, at least a first felt intermediate layer 31, preferably a second felt intermediate layer 32 and a top cloth layer 33. More than two felted layers normally will not be needed. A resilient bonding material 34 covers the bottom and top faces 24 and 25 of the body 20 and quantities of the bonding material 34 are interposed between and coat the opposed surfaces of the layers 30–33 within the laminate to bond the layers 3014 33 together and to help provide the tapered cross section above discussed.

As seen in FIGS. 3 and 6, the layers 31–33 are of varying width. The bottom woven layer 30 is of substantial width, as measured between its convex and concave perimeter edges, and defines the shape, in plan, of the implant 10. The first intermediate felt layer 31 is of less width than bottom layer 30 and the second intermediate layer 32 is of lesser width than the first intermediate layer 31. Whereas the ends of the bottom woven layer 30 are semicircular, the ends of the intermediate felt layers 31 and 32 are generally much narrower and, in the embodiment shown, are pointed. The top woven layer 33 is generally similar in shape and size to the bottom layer 30 but may be slightly narrower in width.

As seen in FIG. 6 (and in broken line in FIG. 3), the layers 30–32 stacked one atop the other with the central portions of their convex perimeter edges vertically stacked and their ends and concave perimeter edges stepped progressively inboard. Due at least in part to its slope, the top cloth layer 33 preferably has its ends and concave perimeter edge slightly stepped inward from the corresponding edges of the bottom cloth layer 30, again as indicated in FIGS. 3 and 6.

This varying width of the layers and stepping of the ends and concave perimeter edges of the layers, along with the initial flowability of the resilient bonding material 34, determines the wedge shaped cross section of the implant 10.

A porous tube 40 (FIG. 9), preferably of knitted fiber, may be of any desired hollow cross section, for example circular cross section. However, in the preferred embodiment shown, the tube 40 is of generally rectangular cross section, having four evenly circumferentially spaced crimped corners 41 integrally connecting the edges of four side walls 42. The tube 40 is however soft and pliable, and thus is readily deformable in shape. The porous material of the tube permits fibrous tissue grown by the patient to enter the adjacent open mesh of the side wall 42 and crimp corners 41 for interlocking the tube with the adjacent tissue of the patient in a manner more fully discussed hereafter.

Resilient bonding material 43 fixes one side wall 42' (FIGS. 2, 8 and 9) of the tube 40 to the relatively thick central portion of the convex perimeter edge 23 of the body 20. The tube 40 follows the convex perimeter edge 23 through about 180 to 200° of arc and is located symmetrically with respect thereto. The ends of the tube 40 are preferably trimmed at an angle, as indicated at 44 (FIGS. 1 and 8), so that the angle cut open ends 44 of the tube 40 lie substantially tangentially with respect to the curved, convex perimeter edge 23 of the body as the latter approaches the ends 21 of the body. In this way, the ends of the tube 40 blend smoothly into the shape of the body near the ends 21 thereof.

Preferably a high tensile strength tape 50 (FIGS. 1, 2 and 10) of woven fibers extends loosely through the tube 40 and has end portions extending considerably beyond the tube 40 and body 20 for purposes appearing hereafter.

While other materials may be employed, in the preferred embodimentshown, the following materials were found satisfaotory.

Thus, the woven bottom and top cloth layers 30 and 33 were cut from commercially obtained sheets of woven polyester (e.g. Dacron TM) cloth. The woven Dacron cloth is relatively thin, having a thickness approximately comparable to writing paper. The woven polyester fabric used in one unit made according to the invention was of a type already made for implantation in the cardiac field, e.g. for peri-cardium patches.

Also, the felt layers 31 and 32 were of felt-like material of matted polyester (e.g. Dacron TM or Teflon TM) material which is very soft and fluffy and whose surface has a fuzzy, fleece-like texture. The felt layers 31 and 32 are several times thicker than the woven fabric layers 30 and 33. In one unit constructed according to the invention, the felted layers, prior to coating, were of thickness approximately equal to or somewhat exceeding 1/16".

The above-mentioned woven and felted fabrics (at 30–33) are for example available from Meadox, located at Oakland, N.J., under the respective model nos. 019254 and 019304, 019306, 019314, 019316, 019324, and 019326.

Also, the tube 40 was knitted in a continuous length tubular configuration from polyester (e.g. Dacron TM) fiber of approximately one-quarter inch diameter. A suitable tube is available from Meadox located at Oakland, N.J. under model no. 130-10.

Also, the tape 50 was of high tensile strength, woven polyester (e.g. Dacron TM) fiber. In the embodiment shown, the tape was about one-eighth inch wide and had a tensile load rating of about 150 pounds. Suitable tape can be obtained from Meadox located at Oakland, N.J. under model no. 130-20.

Also, the resilient bonding material employed was a polyurethane liquid used as a coating to bond to the above-discussed components (as detailed further hereafter), the coated members then being subjected to a curing step to remove the curing agent (dimethuracedimide) by subjecting the coated member to a special environment of controlled temperature and humidity in a conventional manner. Polyurethane bonding material marketed under the trademark Surethane, available from Cardiac Control Systems located at Palm Coast, Florida has been found suitable.

The cured polyurethane forms a smooth layer which tends to reject patient fiber ingrowth and tends to be, when coated with body liquids present in joints, slippery and of low friction, to simulate the similar characteristics of the natural meniscus cartilage.

Although dimensions may be varied at will to suit the needs of a particular patient cartilage to be replaced, in one particular medial meniscus cartilage constructed according to the invention, the length of the body 20 (measured horizontally in FIG. 1) was about one and three-quarter inches, the maximum width thereof (measured along the vertical cutting line II—II in FIG. 1) was about one-half inch and the shape was generally that shown in FIG. 1, the thickness of the body 20 at its convex perimeter edge 23 maximum thickness being about 3/16".

A favored method of manufacturing an implant 10 according to FIG. 1 is as follows.

The flat, generally C-shaped layers 30–33 of woven fabric and matted material are cut to desired size and shape (depending on the size range and configuration of the type of natural cartilage to be replaced).

In making one unit, the woven bottom layer 30 was coated at least once (preferably twice) with the resilient bonding material 34, being cured after each coating. Unless otherwise stated hereafter, the coated layer (and the partial laminate formed as hereafter described) is laid flat during curing since it tends after curing to return resiliently to the shape (bent or flat) in which is maintained during curing. Curing was carried out by a conventional polyurethane curing method, in a conventional polyurethane curing chamber in which temperature and humidity are conventionally controlled.

Thereafter the top face of the bottom layer 30 was coated once again with the resilient bonding material and the first felt layer 31 was placed thereon in the manner generally indicated in dotted lines in the bottom portion of FIG. 3, namely with the central convex edges of the layers vertically aligned. The resulting initial laminant 30, 31 was then cured.

Thereafter coating of the resilient bonding material was applied atop the felted layer 31 and the coated surface of the underlying layer 30. The felted intermediate layer 32 was then placed upon the coated layer 31. The resulting partial laminant 30–32 was again subjected to curing of the resilient bonding material.

Thereafter, a coating of resilient bonding material was applied to both sides of the top woven fabric layer 33 and the top woven layer 33 was held in a three dimensional semi-circle shape, much like the shpe of a segment of a rounded bowl, namely with the concave perimeter edge 60 substantially in one plane and the central portion 61 of the convex perimeter edge 62 spaced above the plane of the edge 60 by about the desired thickness of the central portion 26 of the convex perimeter edge 23 of the body 20 to be formed. This was done by pulling the ends of the coated top layer 33 from their normal planar position indicated at 63' in dotted lines in FIG. 7, to a more closely laterally spaced position indicated in solid lines at 63 in FIG. 7 and fixing, by means of pins 64 or the like, such ends 63 to a rigid substrate, such as a styrofoam plank and the result was subjected to curing. After curing the layer 33 tends to hold its thus distorted shape even when the pins 64 are removed and the layer 33 is removed from its substrate 65.

Preferably the layer 33 was given a second coating of resilient bonding material and again cured. During this second cure, the now double coated layer 33 may be once again temporarily secured by the pins 64 to the substrate 65 in its solid line position shown in FIG. 7 so that it more rigidly is fixed in its distorted bowl segment shaped configuration.

Thereafter, a further coating of resilient bonding material 34 was placed atop the upper felted layer 32 and covered the exposed edges of the coated layers 31 and 30. The distorted, three dimensional bowl segment shaped layer 33 was then placed upon the coated underlying layers 30–32, and subjected to another curing step. This produced the generally wedge cross section laminated body 20 of FIG. 6.

The coating penetrates only partway through the thickness of the felt layer so that a central thickness of the felt layer remains fluffy and pliable and substantially free of the resilient bonding material in the finished implant, such that the finished implant is pliable.

Thereafter, a further layer of resilient bonding material was applied to the convex perimeter edge 23 of the body 20 and the long side 42' of the end trimmed (at 44) tube 40 was placed thereagainst. The resulting structure was subjected to curing to firmly bond the tube 40 to the body 20 in the manner illustrated in FIGS. 1 and 2. It will be understood that the resilient bonding material 34 interpenetrates the openings in the knit side wall 42' of the tube 40, so that upon curing of the resilient bonding material to the usual resilient rubbery mass, the filaments of bonding material interpenetrating the openings of the knitted tube wall 42' firmly interlock together the tube 40 and body 20.

Optionally, before the tube 40 is subjected to contact with the resilient bonding material on the body 20, the tape 50 may be inserted through the trimmed tube 40 to extend beyond the ends thereof in the manner shown in FIG. 1. Upon completion of the above described bonding of the tube 40 to the body 20 and curing of the intervening resilient bonding material 34, the tape 50 is thus caused to stay in place along the convex perimeter edge 23. As a practical matter, the resilient bonding material 34, prior to curing, may extend far enough through the opposed tube wall 42' to contact parts of the tape 50 and thereby endwise fix the tape 50 to the body 20. However, such endwise fixing is not essential and it suffices that the tube 40 alone be bonded to the body 20, with the tape 50 free to run longitudinally in the tube 40.

OPERATION

As seen in FIG. 11, the implant 10 here shown is insertable in place of the natural cartilage (here the medial meniscus cartilage) of the patient, to seat upon the top of the tibia 11 and assist in supporting the overlying condyle 13 of the femur. In time, natural fibrous tissue growth will enter the openings in the knitted fabric of the tube 40, such as the top and bottom surface thereof and particularly the lateral outboard facing surface 42" thereof, to firmly hold the implant 10 in place in the joint, while yet permitting a natural degree of sliding movement of the implant 10 with respect to the tibia 11 and condyle 13 during normal flexing of the joint.

Optionally, to help anchor the implant 10 in place during healing and fibrous tissue ingrowth, the surgeon may elect to utilize the exposed ends of the tape 50. This can be done, as shown in FIG. 11, by boring angled holes 70 downward through the top of the tibia 11, to emerge at the sides thereof. The exposed ends of the tape 50 can then be extended down through such holes 70 and be secured, as by conventional surgical staples 71, to the side of the tibia 11, thereby limiting relative movement between the implant 10 and the opposed tibia 11 and condyle 13. If the surgeon decides he does not need to use the exposed ends of the tape 50 for anchoring purposes, he can simply trim same off where they emerge from the ends of the tube 40.

In use, the liquid normally present in the joint of the patient will coat the polyurethane coated and sealed bottom and top faces 24 and 25 of the implant 10 just as it would the corresponding bottom and top faces of a natural medial meniscus cartilage similarly located. The implant 10 will thus interact with the relatively moving tibia 11 and condyle 13 during patient movement of the joint, such as would a natural medial meniscus cartilage.

It will be understood that while the invention has been above disclosed, for illustrative purposes and by way of convenient example, in connection with a replacement for a medial meniscus cartilage in a patient, it is contemplated that the invention will also be applicable to other, more or less similar, cartilage replacement situations.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A soft tissue implant in the form of meniscus cartilage replacement for a patient, comprising:
   a woven cloth bottom layer;
   at least one felt intermediate layer lying atop said bottom layer;
   a woven cloth top layer lying atop said at least one felt layer;
   at least one coating of a resilient bonding material coating said layers, said bonding material being interposed between said layers and fixing same together to form a laminated body, said layers being generally C-shaped in plan, so as to have a concave perimeter edge and an oppositely facing convex perimeter edge spaced across the width of said generally C-shaped body, the convex perimeter edge defining the ends of the generally C-shaped body, said at least one felt intermediate layer having a width less than that of said woven top and bottom layers, and therewith having its concave perimeter edge and ends retracted inboard of the corresponding concave perimeter edge and ends of said woven top and bottom layers, and therewith making the body taper in central cross-section from a thin concave perimeter edge to a much thicker convex perimeter edge, said convex perimeter edge tapering to reduce its thickness toward said ends, said body thus having a generally wedge shaped central cross-section, said woven top layer thereby being distorted to a three dimensional generally bowl shape.

2. The apparatus of claim 1 in which said layers are of polyester fiber and said bonding material is of polyurethane.

3. The apparatus of claim 1 wherein said thin concave perimeter edge is a feather edge.

4. The apparatus of claim 1 in which said felt layer is of a fluffy, random filament, pliable material, said coating penetrating only partway through the thickness of said felt layer so that a central thickness of said felt layer remains fluffy and pliable and substantially free of said bonding material thereby rendering the implant pliable.

5. A soft tissue implant in the form of meniscus cartilage replacement for a patient, comprising:
   a woven cloth bottom layer;
   at least one felt intermediate layer lying atop said bottom layer;
   a woven cloth top layer lying atop said at least one felt layer;
   at least one coating of a resilient bonding material coating said layers, said bonding material being interposed between said layers and fixing same together to form a laminated body, said body having spaced apart ends and a perimeter edge extending between said ends, said body being wedge shaped in central cross-section with greatest thickness in the central portion of said perimeter edge and extending towards the ends of said body;
   an elongate tube of woven fabric extending along said perimeter edge and having one side abutting said perimeter edge and an opposite free side and a layer of resilient bonding material interposed therebetween and bonding said side of said tube to said perimeter edge from said greatest thickness central portion substantially to said ends, said resilient bonding material bonding to said wedge shaped body and being interlocked in the woven material of said tube, said tube having a hollow central portion. extending from end to end thereof, at least the opposite free said tube being free of said resilient bonding material so that the woven material thereof is free to become interlocked with eventual adjacent tissue growth in the patient.

6. The apparatus of claim 5 including a high tensile strength tape extending through said tube and well beyond the ends thereof and forming a pair of temporary ties, said tape having end means capable of being led through holes in adjacent bones of the patient and anchored tightly thereto for holding said body and attached tape in place while awaiting ingrowth of tissue to interlock with said opposite side of said tube.

7. The apparatus of claim 6 in which said body is substantially C-shaped in plan so that said perimeter edge and tube bonded thereto are convexly curved.

8. The apparatus of claim 7 in which the ends of said tube have opposing edge that are angled so as to extend substantially tangent to said convex perimeter edge of said body near the ends thereof.

9. The apparatus of claim 7 in which said generally C-shaped body has also a concave perimeter edge connecting said body ends and which defines the thin end of said wedge shaped cross-section, said concave perimeter being of negligible thickness compared to said perimeter edge opposite thereto and bonded to said tube.

10. The apparatus of claim 7 in which said tube is of knitted polyester and said tape is of polyester.

* * * * *

UNITED STATES PATENT AND TRADEMARK OFFICE
CERTIFICATE OF CORRECTION

PATENT NO. : 4,919,667

DATED : April 24, 1990

INVENTOR(S) : James W. Richmond

It is certified that error appears in the above-identified patent and that said Letters Patent is hereby corrected as shown below:

Column 8, line 64; change "7" to --6--.

Signed and Sealed this

Thirty-first Day of December, 1991

*Attest:*

HARRY F. MANBECK, JR.

*Attesting Officer*     *Commissioner of Patents and Trademarks*